United States Patent
Falck, Jr. et al.

(10) Patent No.: US 7,153,267 B2
(45) Date of Patent: Dec. 26, 2006

(54) OPHTHALMOLOGIC APPLANATION PRISM REPLACEMENT SYSTEM

(75) Inventors: Francis Y. Falck, Jr., Stonington, CT (US); Robert W. Falck, 896 Stonington Rd., Pawcatuck, CT (US) 06379

(73) Assignees: Francis Y Falck, Jr., Mystic, CT (US); Robert W. Falck, Mystic, CT (US)

( * ) Notice: Subject to any disclaimer, the term of this patent is extended or adjusted under 35 U.S.C. 154(b) by 501 days.

(21) Appl. No.: 10/453,253

(22) Filed: Jun. 3, 2003

(65) Prior Publication Data

US 2004/0152966 A1 Aug. 5, 2004

Related U.S. Application Data

(60) Provisional application No. 60/443,698, filed on Jan. 30, 2003.

(51) Int. Cl.
*A61B 3/16* (2006.01)

(52) U.S. Cl. .................. 600/406; 600/405

(58) Field of Classification Search ........... 600/405, 600/406, 398; 359/831
See application file for complete search history.

(56) References Cited

U.S. PATENT DOCUMENTS

| | | | | |
|---|---|---|---|---|
| 3,767,293 A | * | 10/1973 | Baker et al. | 352/78 R |
| 3,913,390 A | * | 10/1975 | Piazza | 600/405 |
| 4,580,559 A | * | 4/1986 | L'Esperance | 606/3 |
| 5,002,057 A | * | 3/1991 | Brady | 600/406 |
| 5,031,622 A | * | 7/1991 | LaHaye | 600/398 |
| 5,070,875 A | | 12/1991 | Falck et al. | 128/645 |
| 5,305,747 A | * | 4/1994 | McNaughton et al. | 600/405 |
| 5,501,217 A | * | 3/1996 | Ishiguro et al. | 600/398 |
| 6,123,668 A | * | 9/2000 | Abreu | 600/405 |
| 6,179,779 B1 | * | 1/2001 | Falck et al. | 600/398 |
| 6,413,214 B1 | * | 7/2002 | Yang | 600/405 |
| 6,471,647 B1 | | 10/2002 | Falck et al. | 600/398 |
| 6,945,936 B1 | * | 9/2005 | Kerr | 600/406 |

OTHER PUBLICATIONS

"Strain Gauge Measurement—A Tutorial", Aug. 1998, © 1998 National Instruments Corporation, pp. 1-12.

* cited by examiner

*Primary Examiner*—Max F. Hindenburg
*Assistant Examiner*—Jonathan Foreman
(74) *Attorney, Agent, or Firm*—Brown & Michaels, PC; Eugene S. Stephens & Associates

(57) ABSTRACT

A replaceable applanation prism for an eye examining instrument is made to be discarded after each use. A bendable tab molded on the prism is deformed by a strain gauge as the prism is inserted into a prism holder, and a signal from the strain gauge is used to verify that a previously unused prism has been inserted into the holder. A microprocessor is programmed to recognize the signal produced by initial deformation of the prism tab so as to proceed with an eye examination only after receiving the strain gauge signal verifying that a previously unused prism has been inserted.

20 Claims, 6 Drawing Sheets

OPHTHALMOLOGIC APPLANATION PRISM REPLACEMENT SYSTEM

This application claims the benefit of U.S. Provisional Application No. 60/443,698, filed on 13 Jan. 2003, which provisional application is incorporated by reference herein.

TECHNICAL FIELD

Eye examining instruments using applanation prisms.

BACKGROUND

It is desirable to discard and replace a tonometer prism after it has contacted and become wetted with tears of a pair of eyes being examined. Discarding used prisms can prevent transfer of bacteria, viruses or prions from one patient to another. For this purpose, our previous U.S. Pat. Nos. 5,070,875, 6,179,779, and 6,471,647 and our pending application Ser. Nos. 09/811,709 and 10/178,987 have suggested a few ways of making tonometer prisms readily replaceable. The desirability of replacing applanation prisms is not limited to tonometers. As revealed in our application Ser. No. 10/178,987, applanation prisms are also useable in ophthalmologic instruments examining eyes for purposes other than tonometry.

SUMMARY

The invention of this application involves an improved form of replaceable prism and a new interaction or interrelationship between a prism and a tonometer or other eye examining instrument arranged to ensure that the prism is replaced after each examination of a pair of eyes. The prism and its interaction with the instrument that holds it are aimed at low cost and simplicity so that prism replacement will not be unduly expensive in material, time or labor. Making prism disposal and replacement convenient and efficient helps ensure that prisms will actually be replaced rather than reused with possible risk to patients.

To accomplish this the invention involves a configuration of a disposable prism that is molded of resin to operate within an applanation instrument having a microprocessor and a prism holder into which the prism is inserted in a way that requires prism replacement before proceeding with an eye examination. The prism has a molded element formed to extend transversely of a direction of insertion of the prism into the holder, and the element is deformable from an initial position to a deformed position as the prism reaches an operating position within the holder. The element is also configured so that its first deformation requires a distinct stress not required for any subsequent deformation. Deformation of the element is accomplished by a strain gauge positioned in the holder to engage the element and produce a signal representing the strain encountered in deforming the element as the prism is inserted into the holder. The microprocessor is programmed to recognize the strain gauge signal representing the first deformation of the element and to proceed with an eye examination only when insertion of the prism into the holder causes the strain gauge to produce the signal representing the first deformation of the element.

DRAWINGS

DETAILED DESCRIPTION

Figure 1:
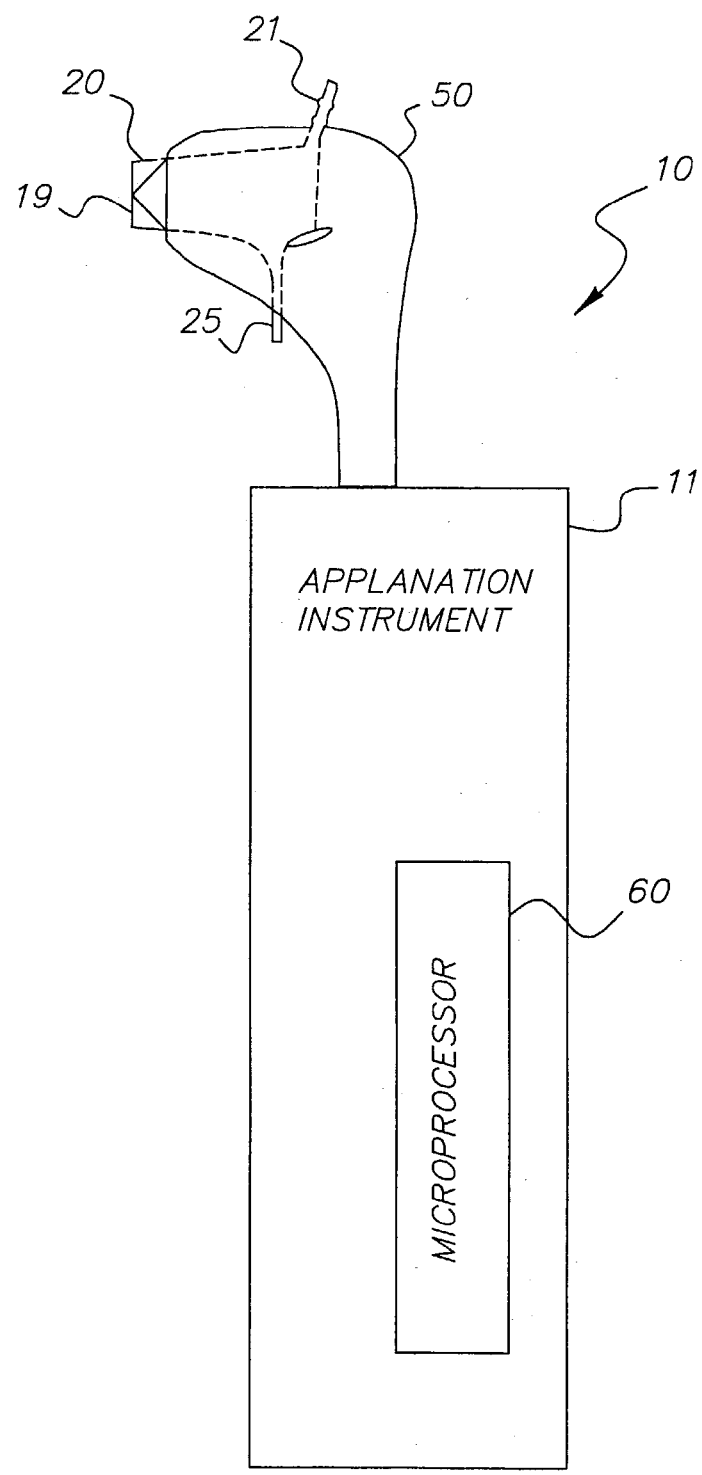
FIG. 1 is a partially schematic elevational view of a preferred embodiment of prism and prism holder combined with a schematically represented applanation instrument.

An eye examining applanation instrument 10, as shown schematically in FIG. 1 includes an applanation prism 20, a prism holder 50 and a microprocessor 60. Instrument 10 can be an applanation tonometer such as disclosed in our previous U.S. Pat. Nos. 5,070,875 and 6,179,779. Applanation prisms and prism holders are also useful in other ophthalmologic eye examining instruments for measuring eye properties other than intra ocular pressure. As explained in our application Ser. No. 10/178,987, such instruments, can use applanation prisms for measuring ocular blood flow, tonography, and different aspects of intra ocular pressure measurements such as systolic pressure, diastolic pressure, and average or mean intra ocular pressure. For purposes of this invention, what is important is not what measurement instrument 10 is being used for, but the configurations and interactions between prism 20, and holder 50.

A body 11 of instrument 10 is schematically illustrated in FIG. 1, because it not only can have many different shapes but also preferably uses different shapes for different purposes. For example, body 11 can have one shape when mounted on and powered by a slit lamp microscope, and can have a different shape configured as a battery powered, hand held portable instrument. Shapes for body 11 made suitable for either of these purposes can also vary widely for other reasons involving materials, costs, and appearance.

Prism 20 is preferably molded of resin material to be inexpensive and thus affordably replaceable. Prism 20 is also configured to be easily inserted into and removed from holder 50 so that discarding prism 20 after each use is convenient as well as affordable. Finally, as explained below, prism 20 and holder 50 are configured so that instrument 10 can reliably determine that a previously unused prism 20 is positioned in holder 50 before proceeding with an eye examination. This ensures that prism 20 is actually replaced for each successive patient.

For ease of insertion and removal, prism 20 preferably has an intregally molded gripping tab 21. An applanation surface 19 of prism 20 should not be touched or handled as a fresh prism is inserted into holder 50, and we prefer that prism 20 have a gripping tab 21 arranged to be handled while inserting and removing prism 20. The position and orientation of gripping tab 21 depends partly on the direction and orientation of the prism insertion and removal motions. Since we prefer lowering prism 20 downward into holder 50 from above, we also prefer that gripping tab 21 be conveniently arranged to extend upward from prism 20. In such a position, tab 21 is disposed to be gripped by a thumb and finger for conveniently pushing prism 20 downward into holder 50, and for lifting prism 20 upward out of holder 50 after it has been used. Gripping tab 21 can also be configured in different ways and arranged in different positions, depending partly upon the most convenient way chosen for inserting and removing prism 20.

The proper location of prism 20 when it is inserted into holder 50 is also important. An improperly seated prism 20 could fail to produce operable results. To prevent this we prefer a prism locating and detenting system that not only ensures proper seating of an inserted prism, but also lets a person inserting the prism know when proper seating has occurred. For these purposes, preferred prism 20 has a location projection 25 that extends downwardly from prism 20 in an opposite direction from gripping tab 21 to locate the prism properly in holder 50. A different position or orientation for projection 25 is also possible, especially for a prism that is inserted into holder 50 in a different way.

Figure 8:
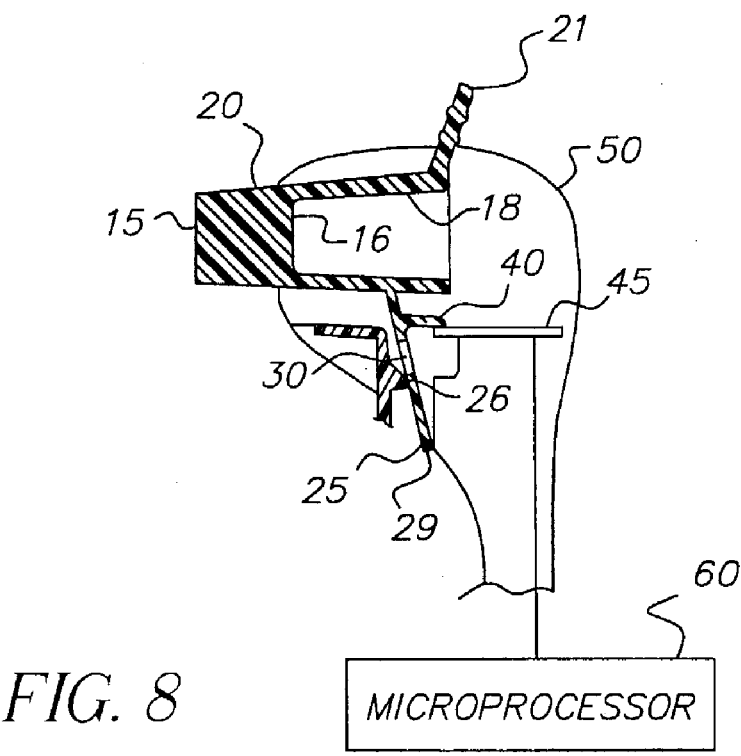
FIG. 8 is a partially schematic and fragmentary cross sectional view of the prism and holder of FIG. 7, showing the prism being inserted part way into the holder.
Figure 9:
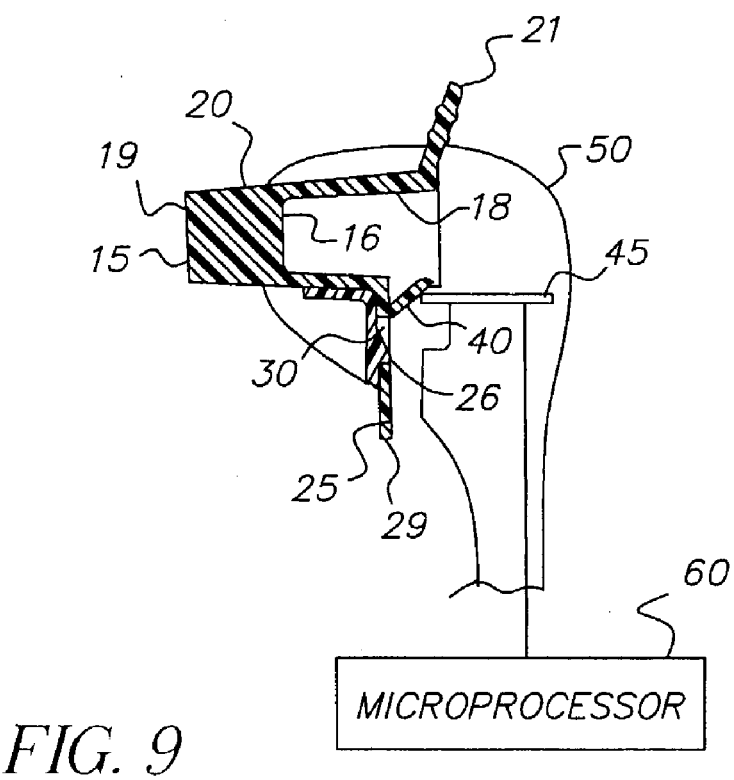
FIG. 9 is a partially schematic and fragmentary cross sectional view of the prism and holder of FIG. 7, taken along the line 9—9 thereof, and showing the prism fully inserted into the holder.

Projection 25 also preferably detents or snap locks into place when prism 20 is properly positioned. FIGS. 8 and 9 best show this action of location tab 25. Prism 20 is shown partially inserted into holder 50 in FIG. 8, where location projection 25 is sliding over detent 26. To ease this motion, detent 26 has a cammed entry surface 27. After prism 20 is fully seated in holder 50, as shown in FIG. 9, an aperture or opening 30 in locator projection 25 snaps over and locks against detent 26 to hold prism 20 firmly in an operating position.

Removing prism 20 after it has been used in examining a pair of eyes requires pulling back on the lower tip 29 of location tab 25 to release its locking engagement with detent 26. Prism 20 can then be lifted out of holder 50 by gripping and pulling upward on tab 21. For prism release purposes, the lower end 29 of location tab 25 preferably extends below the bottom of holder 30, where it is accessible to finger pressure releasing projection 25 from detent 26.

Figure 2:
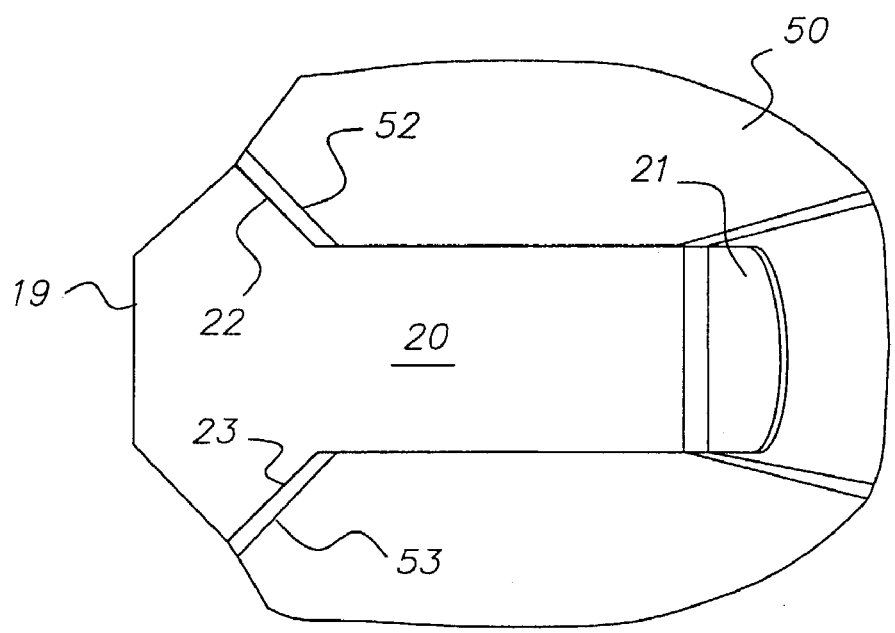
FIG. 2 is a partially schematic plan view of the prism and holder shown in FIG. 1.
Figure 3:
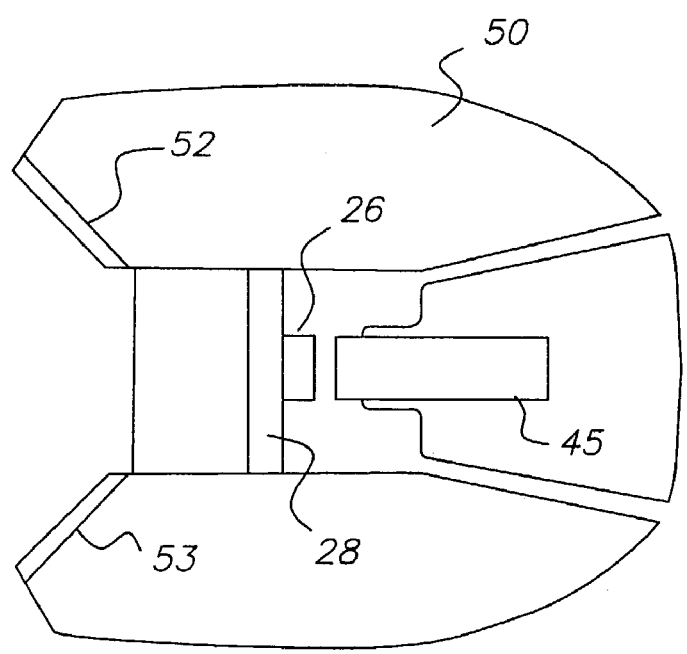
FIG. 3 is a partially schematic plan view of the prism holder as shown in FIG. 2, with the prism removed.
Figure 4:
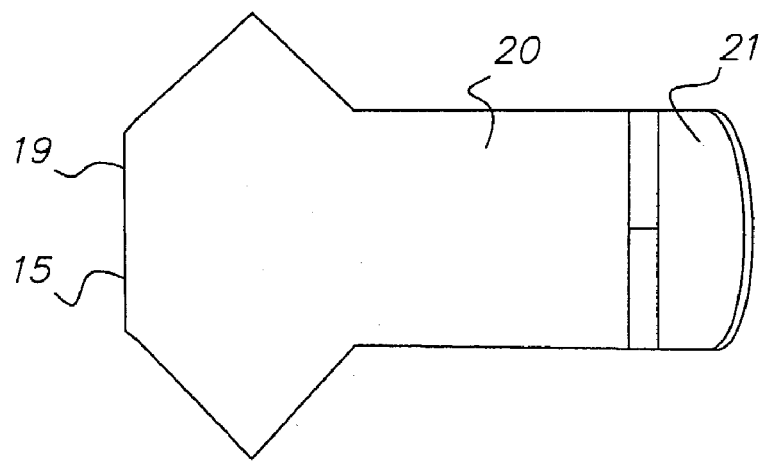
FIG. 4 is a plan view of a preferred embodiment of a prism combinable with a holder shown in FIGS. 2 and 3 and useable with the applanation instrument of FIG. 1.
Figure 5:
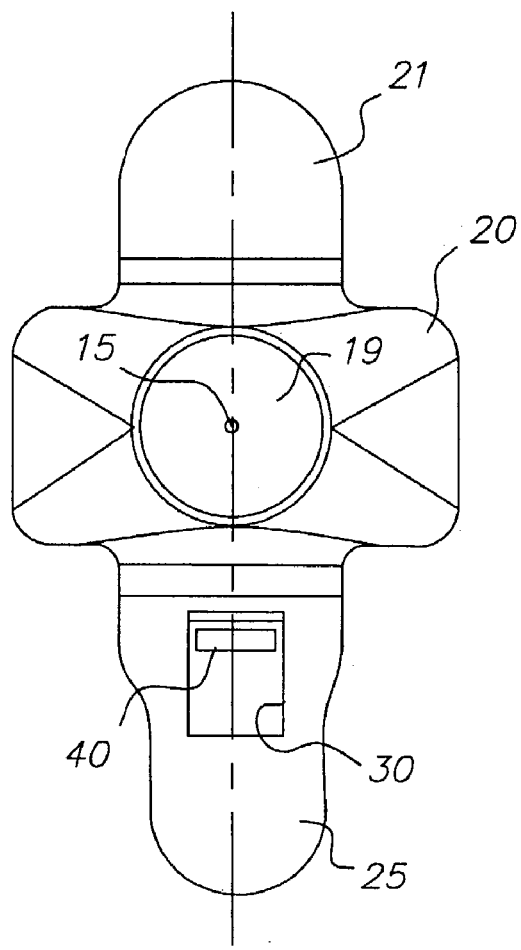
FIG. 5 is a front elevational view of the prism of FIG. 4.
Figure 6:
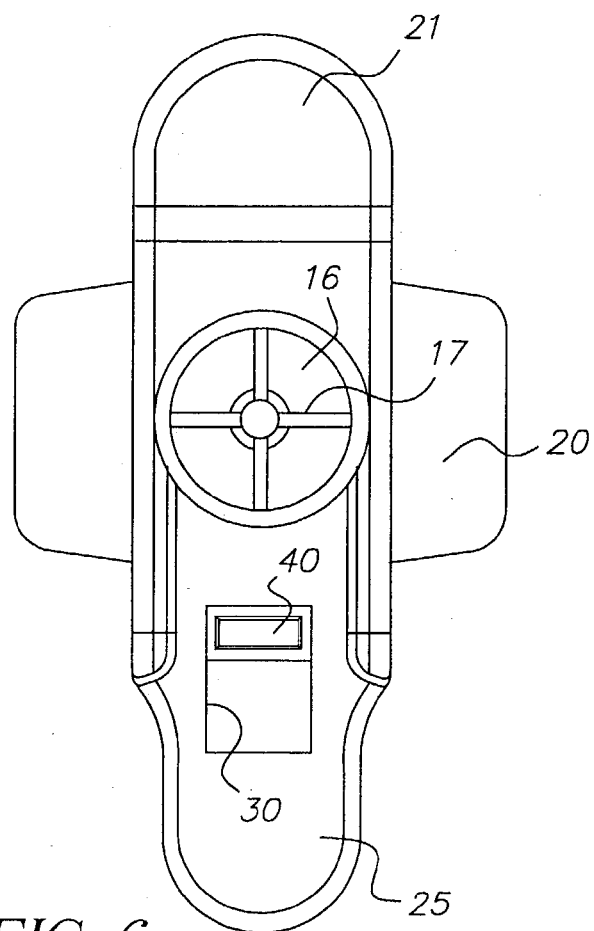
FIG. 6 is a rear elevational view of the prism of FIG. 5.
Figure 7:
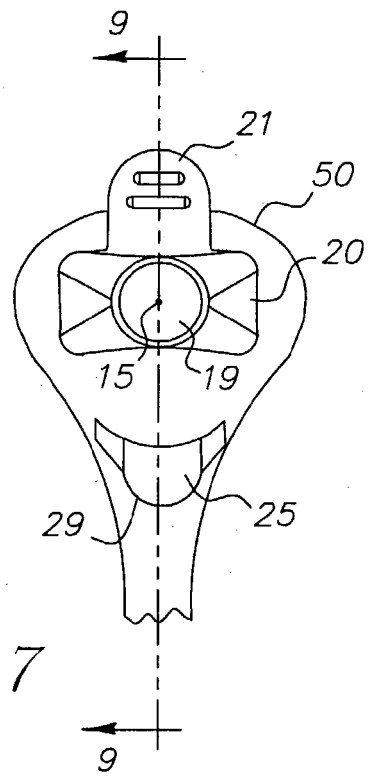
FIG. 7 is a front elevational view of the prism and holder of FIGS. 1 and 2.

A slot 28 in holder 50 containing detent 26 is angled slightly relative to the orientation of tab 25, which urges location projection 25 rearwardly as prism 20 is pushed downwardly into holder 50. This draws prism 20 rearwardly as it is inserted into holder 50 and ensures that prism port surfaces 22 and 23 are drawn snugly and respectively against emitter 52 and detector 53, which are arranged in holder 50 as shown in FIG. 2. Light from emitter 52 can then reliably enter prism port 22 to be incident on applanation surface 19 of prism 20 and be partially reflected to prism port 23 and detector 53. Prism ports 22 and 23 are preferably identical so that emitter 52 and detector 53 can be arranged on either side of prism 20. The amount of light reaching detector 53 depends on the size of an area of cornea applanated by prism surface 19. The operation and affect of such a light path is explained in our previous U.S. Pat. Nos. 5,070,875 and 6,179,779 and in our application Ser. No. 10/178,987.

There are many different ways that a prism 20 can be detented or snap locked into a holder 50, other than the particular detent illustrated. What is preferred for any such arrangement is that a detent be positive and noticeable to a person inserting prism 20, to indicate that the prism is fully inserted into holder 50. It is also preferred that the detenting of the prism into the holder be quick and efficient, both for insertion and removal. The detenting system also preferably urges prism 20 rearwardly to insure that prism port surfaces 22 and 23 engage emitter 52 and detector 53 in prism holder 50 for reliable optical operation. The illustrated interlock between tab 25 and detent 26 accomplishes these objectives, but is clearly not the only plausible solution. Different paths of movement for insertion and removal of prism 20 can lead to different detent systems that accomplish similar objectives.

The interaction between prism 20 and holder 50 of instrument 10 is also preferably arranged to require that prism 20 be replaced after each examination of a pair of eyes. The interaction proposed by this invention, is a new way of accomplishing that. The goal is to preclude instrument 10 from examining a new pair of eyes until a new prism 20 is inserted into holder 50.

The preferred prism replacement requirement is met by a deformable element 40 intregally formed on prism 20 to extend transversely of the path of movement followed by prism 20 as it is inserted into holder 50. Interacting with deformable tab 40 is a strain gauge 45 mounted in holder 50 and communicating with microprocessor 60 in instrument 10. As prism 20 is inserted into holder 50, deformable tab 40 encounters strain gauge 45, as shown in FIG. 8. As prism 20 proceeds from a partially inserted position shown in FIG. 8 to a fully inserted position shown in FIG. 9, deformable tab 40 is bent from an initial position shown in FIG. 8 to a deformed position shown in FIG. 9. The bending of deformable element 40 requires stress supplied by the person pushing downward on grippable tab 21 in the course of pushing prism 20 down into holder 50. Such a stress force is preferably minor and easily achieved by the person inserting prism 20.

Strain gauge 45, which engages and requires deformation of element 40 as prism 20 is inserted into holder 50 produces a signal representing the strain encountered in bending tab 40. This signal is delivered to microprocessor 60, which is programmed to recognize a strain signal produced by an initial bending of deformable element 40. Any subsequent bending of element 40 requires a different and preferably reduced strain on gauge 45, which then produces a distinguishably different signal to microprocessor 60. By this arrangement, instrument 10 is able to recognize reliably the insertion of a previously unused prism 20 into holder 50, because of the distinct signal produced by strain gauge 45 encountering a never previously deformed tab 40. Microprocessor 60 is then programmed to proceed with an eye examination only after receiving the appropriate signal from strain gauge 45 indicating that an unused prism 20 has been inserted into holder 50.

Figure 10:
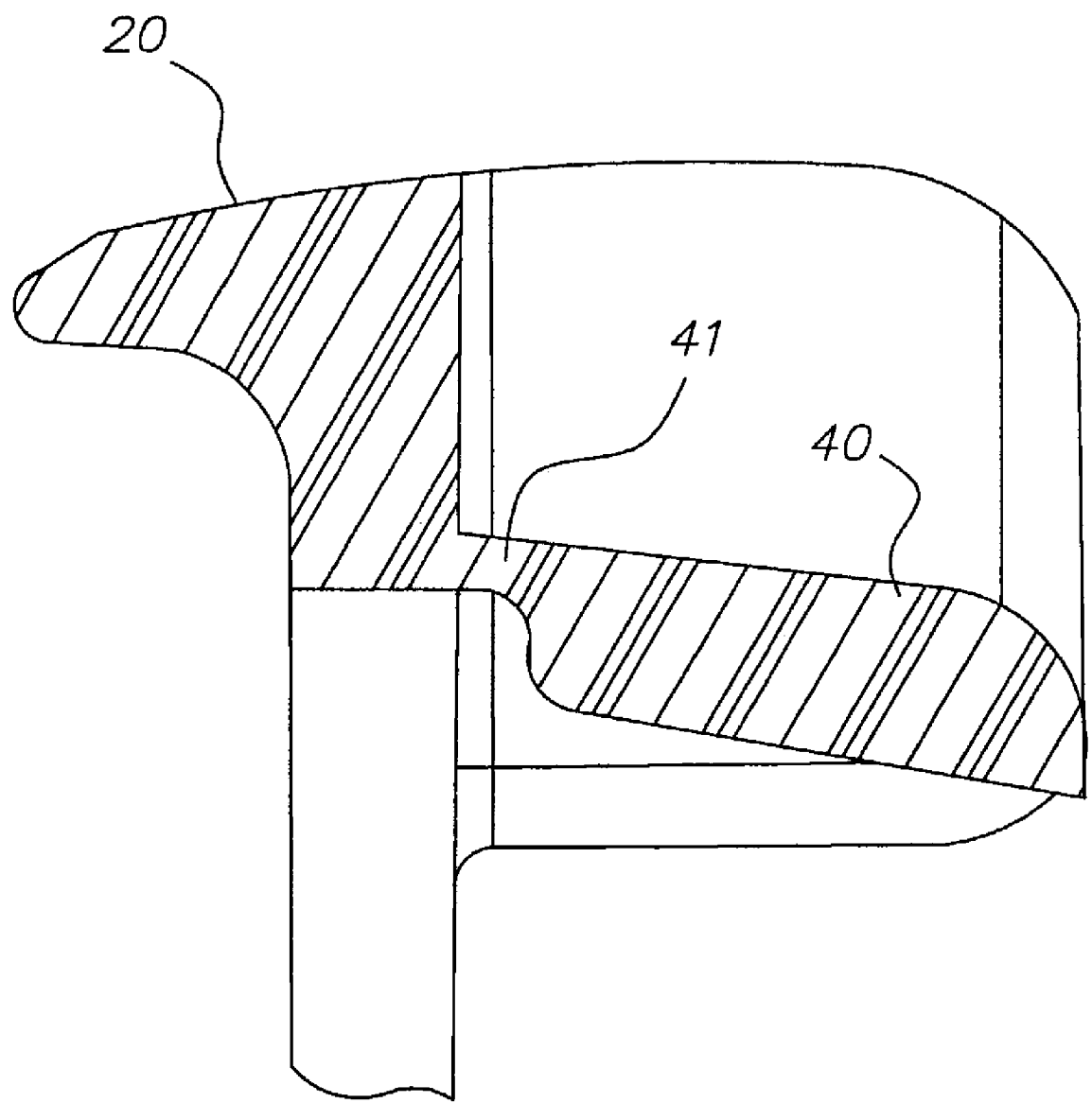
FIG. 10 is an enlarged, fragmentary cross sectional view of a preferred embodiment of a deformable element for the prism of FIGS. 4–6.

A preferred way of configuring deformable element 40 so that its initial deformation produces a distinct signal from strain gauge 45 is to mold element 40 with a thin hinge connection 41 to prism 20, as best shown in the enlarged fragmentary view of FIG. 10. Initial bending of element 40 then requires more stress than any subsequent bending of element 40, and this in turn exerts a distinctive strain on gauge 45 during the initial bending of tab 40. Experiments have shown that tape, glue, and other reinforcements of an already-bent tab 40 do not succeed in restoring tab 40 to its initial condition and its initial ability to produce the initial strain signal from gauge 45. From this it appears that the deformable element and strain gauge combination for a prism replacement requirement cannot be easily defeated.

An advantage of deformable element 40 and strain gauge 45 is that element 40 is not broken away from prism 20 as it is bent during prism insertion. Having a prism element break off and leave a separate piece loose within holder 50 is undesirable, as likely to interfere with operations of holder 50.

Another advantage of deformable element 40 is that it is preferably molded integrally with prism 20. Experiments have shown that polymers having the desired optical properties for prism 20 can also provide deformable element 40 so that it co-operates successfully with strain gauge 45, as explained above. This helps make prism 20 inexpensive, which in turn is desirable to make its discard and replacement affordable.

Deformable elements usable in co-operation with a strain gauge to determine that a replaced prism has not been previously used can also be arranged in other ways. One configuration we prefer is that the deformable element extends in a direction transverse to the direction of insertion of prism 20 into holder 50. Changing the direction of the path followed by prism 20 as it is inserted into holder 50 then changes the preferred direction of orientation of any deformable element. This in turn would change the position of strain gauge 45. It is also not essential that deformable element 40 be a bendable tab, as illustrated. A beam of prism resin material could be integrally connected at each of its ends to prism 20 and be deformable in a central region encountered by a strain gauge. Other variations on deformable elements are possible, such as diaphragms or projections that do not bend as far as illustrated. In addition, there are many ways of ensuring that an initial deformation of a molded element exerts a strain on a gauge distinctively different from any subsequent deformation of the element. For example, a bendable element could have a thin molded prism connection that breaks in one region to allow deformation of another connection that does not break. We prefer that any deformable element be integrally molded with prism 20, rather than requiring a separate construction attached to prism 20. Although separately fabricated elements could be made to co-operate successfully with a strain gauge, separate constructions generally cost more and would tend to increase the cost of prism 20.

Prism 20 is also improved in several other respects. It preferably has a hollow rear region 18, as best shown in FIGS. 8 and 9, to reduce the amount of material required and simplify the molding requirements for prism 20. Prism 20 is also preferably made so that an operator can see or sight through prism 20 to guide it as it approaches a cornea of an eye. For such sighting purposes, rear face 16 of prism 20 is formed with a reticle 17 identifying a sighting center or prism axis extending through prism 20. The applanation face 19 of prism 20, which is generally flat, is then provided with a small central indent 15 on the optical or sighting axis through prism 20. Indent 15 does not internally reflect light to detector 53 and thus produces a small dark spot on the front face 19 of prism 20. A viewer sighting through prism 20 can then center the dark spot caused by indent 15 within reticle 17 to verify proper alignment of prism 20 as it approaches the optical center of a cornea of an eye. Indent 15 and reticle 17 are each formed integrally with prism 20 as it is molded so that neither requires any add on parts. From the patient's point of view, indent 15 on applanation surface 19 appears as a small bright spot. This helps the patient fixate on the center of applanation surface 19 as the prism approaches the eye. The prism's sight-through feature for the instrument operator and bright spot fixation feature for the patient, cooperate to help insure accurate coaxial alignment of the eye and the prism.

We claim:

1. A system ensuring replacement of a molded resin prism used in an applanation tonometer having a microprocessor and a holder for receiving the prism in an operating position, the system comprising:
   a. the prism being molded to form a bendable tab having an initial position extending transversely of a direction of insertion of the prism into the holder;
   b. a strain gauge arranged in the holder to engage the tab as the prism is being inserted into the holder and before the prism reaches the operating position;
   c. the strain gauge being arranged to bend the tab from its initial position to a bent position as the prism is moved fully into the holder to the operating position;
   d. the strain gauge being arranged to produce a tab bending signal delivered to the microprocessor representing the strain involved in bending the tab from its initial position to its bent position;
   e. the tab being configured so that a first bending of the tab from its initial position to its bent position requires more stress than any subsequent bending of the tab from its initial position to its bent position;
   f. the microprocessor being programmed to distinguish between a tab bending signal from the strain gauge representing the first bending of the tab and a tab bending signal from the strain gauge representing the subsequent bending of the tab; and
   g. the microprocessor being programmed to proceed with an eye examination only if a prism inserted into the holder causes the strain gauge to produce a tab bending signal representing the first bending of the tab.

2. The system of claim 1 wherein the prism has a location projection that detents in the holder when the prism is in the operating position.

3. The system of claim 1 wherein an optical axis region of an applanation surface of the prism has a small indent.

4. The system of claim 1 wherein a rear face of the prism has a reticule on an optical axis of the prism.

5. An applanation tonometer having a microprocessor and a prism holder combined with a molded resin prism insertable into the holder in a way that requires prism replacement before proceeding with an eye examination, the combination comprising:
   a. the prism being molded with an element formed to extend transversely of a direction of insertion of the prism into the holder;
   b. the element being deformable from an initial position to a deformed position as the prism is inserted into the holder to reach an operating position within the holder;
   c. the element being configured so that a first deformation of the element requires more stress than any subsequent deformation of the element;
   d. the holder including a strain gauge positioned to engage and deform the element as the element is inserted into the holder;
   e. the strain gauge being arranged to produce a signal representing the strain encountered in deforming the element as the prism is inserted into the holder;
   f. the microprocessor being programmed to recognize the strain gauge signal representing the first deformation of the element;
   g. the microprocessor being programmed to proceed with an eye examination whenever insertion of a prism into the holder causes the strain gauge to produce the signal representing the first deformation of the element; and
   h. the microprocessor being programmed not to proceed with an eye examination whenever insertion of a prism into the holder causes the strain gauge to produce a signal distinguishably different from the signal representing the first deformation of the element.

6. The combination of claim 5 wherein the prism has a locator projection that seats in the holder in a detented position when the prism is in its operating position.

7. The combination of claim 5 wherein the prism has a gripping tab by which the prism is inserted into the holder.

8. The combination of claim 5 wherein an optical axis of the prism intersects a reticule on a rear face of the prism and an indentation on an applanation surface of the prism.

9. A method of insuring that a molded resin prism is replaced in an applanation tonometer before each eye examination, the method comprising:
   a. forming prism replacements that each have a tab that is initially deformable in response to a predetermined stress;
   b. inserting one of the prism replacements into a prism holder of the tonometer so that the deformable tab engages a strain gauge in the holder and becomes deformed by the strain gauge as the prism is moved into an operating position within the tonometer;
   c. arranging the strain gauge to produce a signal representing the strain encountered in initially deforming the tab as the prism is inserted into the holder;
   d. transmitting the strain gauge signal to a microprocessor in the tonometer and programming the microprocessor to recognize the strain gauge signal representing the initial deformation of the tab; and
   e. programming the microprocessor to proceed with an eye examination only upon receiving the strain gauge signal representing the initial deformation of the tab.

10. The method of claim 9 including programming the microprocessor not to proceed with an eye examination and to indicate to the tonometer user upon receiving a strain gauge signal distinguishably different from the strain gauge signal representing initial deformation of the tab.

11. A method of insuring that an applanation tonometer prism is replaced before each examination of a pair of eyes, the method comprising:
   a. molding the prism of resin with a deformable element that is deformable to a predetermined extent without breaking away from the prism;
   b. configuring the deformable element to have an initial resistance to an initial deformation to the predetermined extent and a reduced resistance to any subsequent deformation to the predetermined extent;
   c. arranging a strain gauge within the tonometer to measure deformation resistance of the deformable element;
   d. arranging the strain gauge to produce a strain signal delivered to a microprocessor in the tonometer as representative of the deformation resistance of the deformable element; and
   e. programming the microprocessor to proceed with the examination of the pair of eyes only when the strain signal coincides with the strain representing the initial resistance.

12. The method of claim 11 including programming the microprocessor not to proceed with the examination of the pair of eyes and to indicate to the tonometer user when the strain signal the distinguishably differs from the strain representing the initial resistance.

13. A tonometer and applanation prism combined to ensure replacement of the prism before proceeding with examination of a pair of eyes, the combination comprising:
   a. the prism having a deformable element configured to have a larger resistance to an initial deformation and a smaller resistance to a subsequent deformation;
   b. the tonometer having a strain gauge arranged to cause deformation of the deformable element as the prism is inserted into the tonometer;
   c. a microprocessor in the tonometer receiving a deformation signal from the strain gauge and being programmed to recognize an initial deformation signal corresponding to the strain encountered during the initial deformation of the deformable element; and
   d. the microprocessor being programmed to proceed with the examination of the pair of eyes only upon receiving the initial deformation signal.

14. The combination of claim 13 wherein the deformable element is a bendable tab oriented transversely to a direction of insertion of the prism into the tonometer.

15. The combination of claim 13 wherein the deformable element is configured not to break away from the prism.

16. The combination of claim 13 wherein the prism includes a location projection that snap fits into a seated position when the prism is in an operating position within the tonometer.

17. A disposable molded resin prism usable in an applanation tonometer, the prism comprising:
   a. a bendable tab formed of the molded resin of the prism to extend from a body of the prism;
   b. the tab being configured to be bent from an initial position to a bent position as the prism is inserted into the tonometer;
   c. the tab being formed to survive bending without breaking off from the prism body during insertion of the prism into the tonometer and removal of the prism from the tonometer for disposal; and
   d. the tab being formed to have a resistance to an initial bending that is larger than any resistance of the tab to a subsequent bending.

18. The prism of claim 17 wherein the tab is formed with a thin hinge line allowing the tab to bend.

19. The prism of claim 17 wherein the tab extends from a non-optical surface of the prism body.

20. A tonometer applanation prism and prism holder comprising:
   the prism being molded of resin material and having a positioning projection extending approximately in a direction of insertion of the prism into the holder;
   the positioning projection and holder being configured to interact in a detent that engages as the prism reaches an operating position within the holder; and
   the detent between the positioning projection and the holder being effective when engaged to hold the prism against withdrawal from the operating position;
   the positioning projection is configured to flex as the positioning projection engages the detent;
   flexing of the positioning projection within the holder as the detent engages draws the prism into engagement with an emitter and a detector in the holder; and
   the positioning projection is arranged to be manually flexed to release the engaged detent, which causes the prism to spring back to a position short of the operating position.

* * * * *